United States Patent
Fenchel et al.

(10) Patent No.: US 9,778,382 B2
(45) Date of Patent: Oct. 3, 2017

(54) MOTION-CORRECTED PET IMAGES

(71) Applicant: SIEMENS AKTIENGESELLSCHAFT, Munich (DE)

(72) Inventors: Matthias Fenchel, Erlangen (DE); Ralf Ladebeck, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1248 days.

(21) Appl. No.: 14/043,114

(22) Filed: Oct. 1, 2013

(65) Prior Publication Data

US 2014/0243653 A1    Aug. 28, 2014

(30) Foreign Application Priority Data

Oct. 8, 2012 (DE) ......................... 10 2012 218 289

(51) Int. Cl.
*A61B 5/05* (2006.01)
*G01T 1/29* (2006.01)
(Continued)

(52) U.S. Cl.
CPC ............ *G01T 1/2985* (2013.01); *A61B 5/055* (2013.01); *A61B 5/113* (2013.01); *A61B 5/7285* (2013.01);
(Continued)

(58) Field of Classification Search
CPC ... G01T 1/2985; A61B 6/5247; A61B 6/4417; A61B 6/5264; A61B 6/037;
(Continued)

(56) References Cited

U.S. PATENT DOCUMENTS

2008/0137930 A1* 6/2008 Rosen ................... G06T 11/005
                                                       382/131
2009/0037130 A1    2/2009 Feiweier et al.
(Continued)

FOREIGN PATENT DOCUMENTS

DE        102007034955 A1    2/2009

OTHER PUBLICATIONS

Thorsten Rohlfing et. al Modeling liver motion and deformation during the respiratory cycle using intensity-based free-form registration of gated MR imgages; Department of Neurological Surgery, Department of Radiation Oncology, Department of Radiology, University of Rochester, Rochester NY; Proceedings of SPIE, 2001, p. 337-348, vol. 4319.

(Continued)

*Primary Examiner* — Sanjay Cattungal
(74) *Attorney, Agent, or Firm* — Harness, Dickey & Pierce, P.L.C.

(57) ABSTRACT

A method is disclosed for generating a motion-corrected PET image of an examination area in a combined MR-PET system. In an embodiment, the method includes recording PET events from the examination area in a first recording time frame; recording a number of MR images of the examination area in at least the first recording time frame; calculating an at least two-dimensional movement information of the examination area on the basis of the number of MR images, wherein the movement information describes the movement information of the examination area during the first recording time frame, and determining the motion-corrected PET image from the PET events using the calculated movement information.

10 Claims, 4 Drawing Sheets

(51) Int. Cl.
| | |
|---|---|
| A61B 5/00 | (2006.01) |
| A61B 5/055 | (2006.01) |
| A61B 5/113 | (2006.01) |
| A61B 6/03 | (2006.01) |
| A61B 6/00 | (2006.01) |
| G01R 33/48 | (2006.01) |

(52) U.S. Cl.
CPC ............ A61B 6/037 (2013.01); A61B 6/4417 (2013.01); A61B 6/5247 (2013.01); A61B 6/5264 (2013.01); G01R 33/481 (2013.01); A61B 5/0035 (2013.01); A61B 6/527 (2013.01)

(58) Field of Classification Search
CPC ....... A61B 5/7285; A61B 5/055; A61B 5/113; A61B 5/0035; A61B 6/527; G01R 33/481
USPC .......................... 600/407–430; 382/128–132
See application file for complete search history.

(56) References Cited

U.S. PATENT DOCUMENTS

2010/0106004 A1* 4/2010 Harvey ............ G01R 33/56509
600/411
2010/0268063 A1* 10/2010 Schmidt ............... G01R 33/481
600/411
2010/0290683 A1* 11/2010 Demeester ............. A61B 6/037
382/131

OTHER PUBLICATIONS

German Priority Document for German Application 10 2012 218 289.6.
German Office Action for German Application 10 2012 218 289.6 dated Jun. 18, 2013.

* cited by examiner

MOTION-CORRECTED PET IMAGES

PRIORITY STATEMENT

The present application hereby claims priority under 35 U.S.C. §119 to German patent application number DE 102012218289.6 filed Oct. 8, 2012, the entire contents of which are hereby incorporated herein by reference.

FIELD

At least one embodiment of the invention generally relates to a method for generating a motion-corrected PET image of an examination area in a combined MR-PET system and a MR-PET system herefor.

BACKGROUND

The measurement of PET images of an examination area typically requires measuring times in the range of minutes. As a result, moving body parts can only be measured out of focus. One possibility of improving the focus in the generated PET images resides in using the so-called gating. With cyclical movements such as for instance respiratory movement or heart movement, the overall measuring time available is divided into individual phases of the movement. In order to create the PET image, only the PET events which occur in a specific phase of the movement are taken into account. A sharp image, i.e. an image without motion artifacts, is herewith achieved. The price for this is however a reduced signal-to-noise ratio, since the measuring time per image is reduced. It is not necessary in many application instances to temporally resolve the movement of an organ in the examination area, but it is instead more important for instance to be able to identify a lesion in the organ. An image with an optimized signal-to-noise ratio is nevertheless required herefor. It can however only be achieved by lengthening the measuring time.

SUMMARY

At least one embodiment of the present invention is directed to improving the PET image measured in a specific measuring time such that the signal-to-noise ratio is improved.

Further embodiments are described in the dependent claims.

According to a first aspect of an embodiment of the invention, a method is provided for generating a motion-corrected PET image of an examination area in a combined MR-PET system. In a first step of the method, PET events from the examination area are recorded in a first recording time frame. Furthermore, a number of MR images of the examination area are recorded in the at least first recording time frame. An at least two-dimensional item of movement information of the examination area is then calculated on the basis of the number of MR images. The movement information here describes the movement of the examination area during the first recording time frame. The motion-corrected PET image is then determined from the PET signals and by taking account of the calculated movement information. It is possible in accordance with the invention to determine the movement of the examination area in the first recording time frame with the high resolution of the MR images compared with PET images.

An embodiment of the invention further relates to a combined MR-PET system, which can generate the motion-corrected PET image. This comprises inter alia a PET unit for recording the PET events from the examination area in the first recording time frame and an MR unit for recording the number of MR images. A computing unit is furthermore provided, which calculates at least two-dimensional movement information of the examination area on the basis of the number of MR images. The computing unit can also determine the motion-corrected PET image from the PET events using the calculated motion information.

BRIEF DESCRIPTION OF THE DRAWINGS

Embodiments of the invention are explained in more detail below with reference to the appending drawings, in which.

DETAILED DESCRIPTION OF THE EXAMPLE EMBODIMENTS

Figure 1:
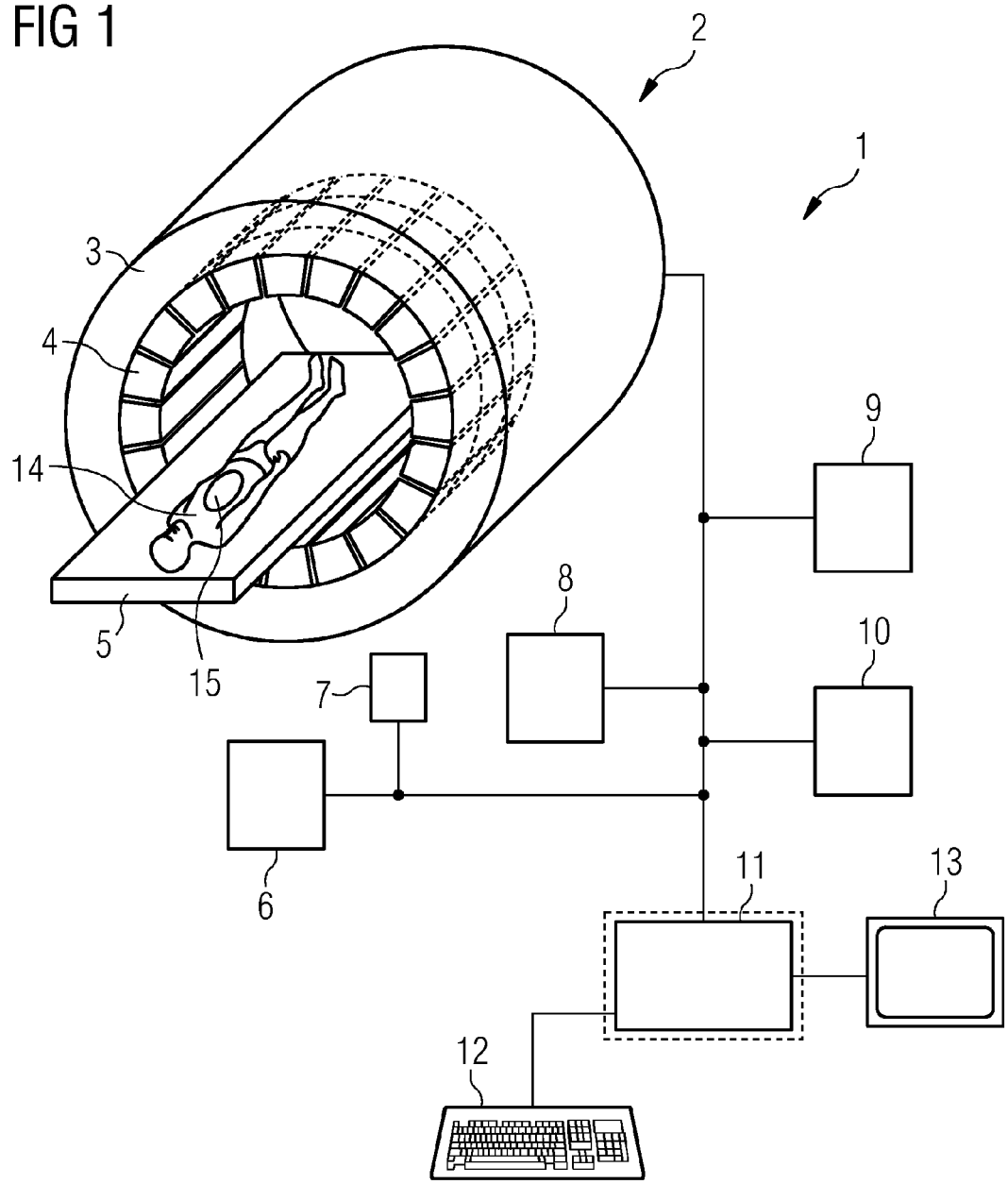
FIG. 1 shows a schematic representation of a combined MR-PET system according to an embodiment of the invention.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to a first aspect of an embodiment of the invention, a method is provided for generating a motion-corrected PET image of an examination area in a combined MR-PET system. In a first step of the method, PET events from the examination area are recorded in a first recording time frame. Furthermore, a number of MR images of the examination area are recorded in the at least first recording time frame. An at least two-dimensional item of movement information of the examination area is then calculated on the basis of the number of MR images. The movement information here describes the movement of the examination area during the first recording time frame. The motion-corrected PET image is then determined from the PET signals and by taking account of the calculated movement information. It is possible in accordance with the invention to determine the movement of the examination area in the first recording time frame with the high resolution of the MR images compared with PET images.

When calculating the motion-corrected PET image from the PET events, the movement can then be determined and taken into account such that the movement of the examination area is corrected and a motion-corrected PET image is calculated. It is herewith possible to take the PET events into account even during the various positions during the movement of the examination area. All PET events counted during a recording time frame can essentially be used for generating the motion-corrected PET image, and not only the PET events which were detected during a specific movement state. The MR images are used to correct the movement arising so that the PET events which took place during the movement can also be taken into account.

The movement of the examination area is preferably a cyclical movement such as for instance the respiratory movement or the heart movement. In this embodiment, the number of MR images is preferably recorded in various time segments of the cyclical movement, as a result of which an item of movement information is retained in the individual time segments. The movement relative to a reference position of the examination area is herewith preferably determined in individual time segments. With the respiratory movement, this may be the position of the examination area for instance (for instance in the abdomen) which has the examination area at the end of the exhalation phase. It is also possible to use any other reproducible position of the cyclical movement.

It is possible for instance to determine an at least two-dimensional movement segment information of the examination area for each of the time segments, wherein each movement segment information describes the movement of the examination area in the associated time segment. The movement which the examination area has made relative to a reference position can then be determined from the individual MR images in various time segments. Generally the at least two-dimensional movement information can contain a fixed translation of the examination area, a rotation and/or a deformation of the examination area. Depending on the movement that has occurred, a rigid translation, a rotation and/or a deformation can be taken into consideration in the determination of the movement. The movement information can describe the movement in a plane two-dimensionally, or it can be three-dimensional.

In one embodiment it is possible to generate time segment PET images for the different time segments of the cyclical movement, wherein a time segment PET image is generated on the basis of the PET events occurring in the associated time segment. The time segment PET image produced can then be corrected with the associated movement segment information of the associated time segment so that a corrected time segment PET image is produced for each time segment. The movement occurring in the associated time segment is corrected herein. By totaling the individually corrected time segment PET images, it is possible to generate the motion-corrected PET image.

The individual time segment PET images can be weighted equally when forming the total of the corrected time segment PET images for the motion-corrected PET image. In another embodiment, it is possible to implement the total formation as a function of the size of the movement occurring in a sub segment. This means that a time segment PET image is weighted less if the movement in the associated time segment was greater than in another time segment PET image, in which the movement was lower in the associated time segment. This enables potential artifacts which occur if large transformations are needed to take the movement into account in order to generate the time segment PET image to be reduced.

In another embodiment, the time segment PET images are not necessarily generated, but it is instead possible to correct the individual PET events and the local information determined from the PET events such that the movement calculated from the MR images is taken into account. One possibility here is to determine the trajectory of the annihilation radiation associated with the respective PET event, that is followed by said annihilation radiation. With the aid of the at least two-dimensional movement information, corrected trajectories which take the movement of the examination area into account can then be calculated. The motion-corrected PET image can be calculated from these corrected trajectories. In this context it is possible to determine deformed trajectories for the individual events on the basis of the at least two-dimensional movement information which take the respective movement information into account and the movement-corrected PET image is calculated with the aid of the deformed trajectories. The measured PET events can herewith be distributed in accordance with the movement information for instance on new so-called lines of response. A fractional rebinning can herewith be used, which distributes a PET event in accordance with the sum of the movement onto a deformed line of response.

In order to determine the movement in the individual time segments, it is possible to record the MR images with a segmented recording technology, in which the cyclical movement of the examination area is monitored and a raw data space and/or k-space of an MR image belonging to a time segment is then only filled with raw data if a specific movement state of the cyclical movement takes place.

It is furthermore possible to use the number of MR images, which are recorded to determine the at least two-dimensional movement information simultaneously to determine the attenuation correction. The gamma radiation occurring in the PET detectors of the PET unit is attenuated again when passing through the examination area. With the aid of the MR images, this attenuation can be better determined, since, with the aid of the MR images, it can be determined whether and which tissue lies between the source of the radiation and the PET detector. In this embodiment, the recorded MR images can be used for different purposes, firstly for determining the attenuation correction and secondly for the correction of the movement.

An embodiment of the invention further relates to a combined MR-PET system, which can generate the motion-corrected PET image. This comprises inter alia a PET unit for recording the PET events from the examination area in the first recording time frame and an MR unit for recording the number of MR images. A computing unit is furthermore provided, which calculates at least two-dimensional movement information of the examination area on the basis of the number of MR images. The computing unit can also determine the motion-corrected PET image from the PET events using the calculated motion information.

FIG. 1 shows a schematic embodiment of a combined MR-PET system 1. This has a MR-PET unit 2, with a magnet 3 for generating the polarization field B0 and the PET detectors 4. A person to be examined 14 arranged on a couch 5 can be introduced into the combined MR-PET unit 2. The person to be examined, of whom a PET image of the examination area 15 is to be generated, can be injected with radionuclide by way of an injector 6, for instance 18F radioactively marked glucose. A movement detector 7 can detect the movement arising during the examination such as the respiratory movement or heart movement for instance. The movement detector may be an EKG for instance with the heart movement, with the respiratory movement, the movement detector 7 can detect a marking on the person to be examined, or the movement is detected with the aid of the generated MR images, for instance by determining the position of the diaphragm in the MR images. The system further comprises a PET unit 8, which is able to calculate a PET image with the aid of the events detected in the PET detectors 4. As a PET image can be generated from the PET detectors 4 with the aid of the signal, it is essentially familiar to the person skilled in the art and is not described in more detail here.

An MR unit 9 is likewise provided, which produces MR images from the MR signals by a detection coil (not shown). How MR signals can be generated and detected by high frequency pulses for deflecting the magnetization and by switching magnetic field gradients is familiar to the person skilled in the art and is not explained in more detail here. It is likewise known to the person skilled in the art that the two units, the MR unit 9 and the PET unit 8, can be operated in a combined unit, as shown. A control unit 11 is provided to control the entire system. The generated MR or PET images or other control information can be displayed on a display unit 13, wherein a user of the system can control the MR-PET system by way of an input unit 12.

A computing unit 10 calculates a motion-corrected PET image as explained below.

Figure 2:
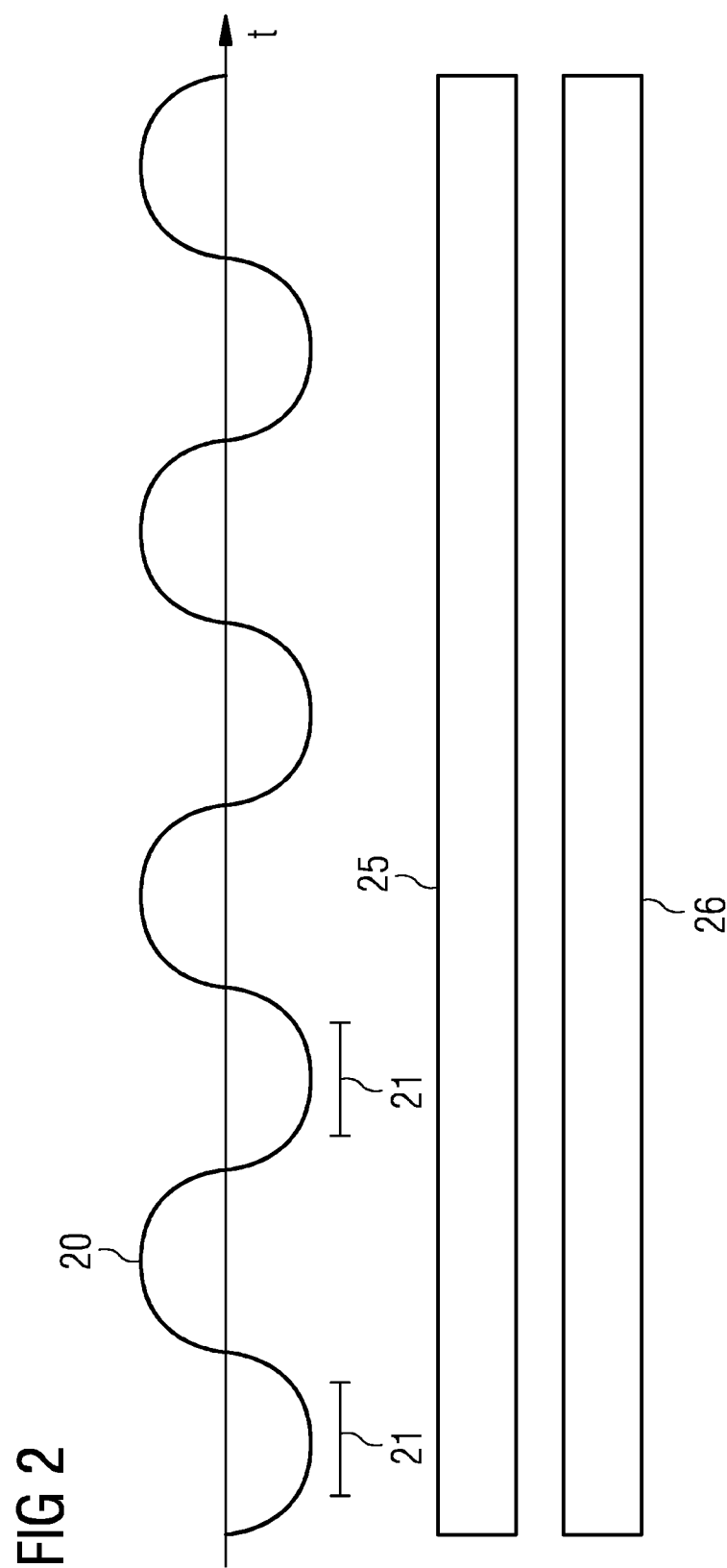
FIG. 2 shows a schematic representation of the cyclical movement of the examination area and the recording of the PET or MR data.

A cyclical movement of the examination area is now shown in FIG. 2, as can occur during the recording of the PET events. In the case shown, the cyclical movement 20 is a respiratory movement for instance as was detected by the movement detector 7. Furthermore, a first recording time frame 25 is shown, during which the PET events are recorded. These PET events during the recording time frame 25 can be stored as a function of time. In this so-called list mode, the individual PET events are stored with the associated time when the PET event took place. By temporal totaling during the first recording time frame 25, PET images can then be generated. According to the prior art, it was possible for instance only to take PET events into account in the time frame 21, here the exhaled state. With a given recording time span, the signal-to-noise ratio is herewith nevertheless lower, since not all PET events can be taken into account or the recording time frame has to be lengthened accordingly in order to be able to take a corresponding number of PET events into account.

As explained below, it is now possible in accordance with the invention to take all PET events into account during the first recording time frame 25. A number of MR images are recorded throughout a second time frame 26. In the example shown, the second recording time frame corresponds to the first recording time frame. The time frame 26 may be longer than the first time frame 25. MR images are however likewise recorded in the first time frame 25.

The recorded MR images can be generated for instance with a segmented recording technology. With this segmented recording technology, the k-space associated with an MR image is only then ever filled with MR signals if a specific movement segment of the cyclical movement takes place. For instance, a segmented gradient echo sequence can be used for the MR imaging.

Figure 3:
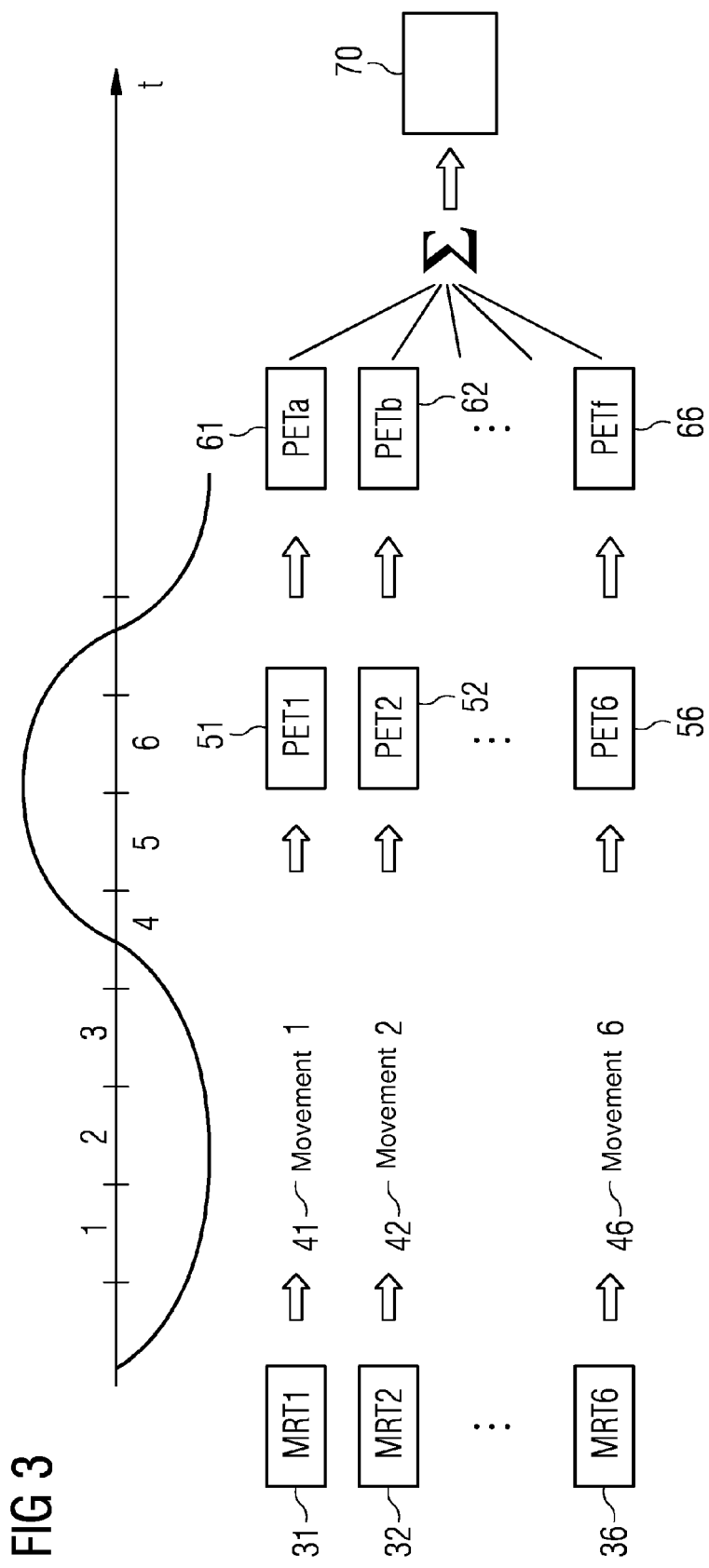
FIG. 3 shows the subdivision of the cyclical movement into individual time segments, wherein PET images of the individual time segments are corrected with the respective movement in the time segments.

With regard to FIG. 3, this means for instance that the movement segment is divided into a number of time segments, in the case shown in FIG. 3, the respiratory movement was subdivided into six different sub segments. The segmented recording technology can now be used such that six different MR recordings 31-36 are recorded for instance, wherein each MR recording only takes signals into account from a specific time segment of the movement. In the case shown, only MR signals are detected and taken into account for instance for creating the MR image 31 if the examination area is located in the second time segment and the MR image 36 only if the examination area is disposed in the time segment 6. It is thus possible to determine the movement of the examination area relative to a reference position.

As a reference position, the position of the examination area and/or the organ contained therein can be at the end of the exhalation cycle, i.e. for instance the time segment 1 in the exemplary embodiment of FIG. 3. For the individual MR images 32-36, the movement relative to this reference position can be determined. The movement may be for instance a translation, rotation and/or deformation. Movement segment information 41-46 can be generated herefrom for each of the time segments. The movement segment information contains in each instance the movement in the associated time segment relative to the reference position. If the time segment 1 is the reference position for instance, then the movement segment information 41 is zero and the other movement segment information 42-46 describes the movement of the examination area relative to the position of the examination area, which it holds during the time span 1. Upon selection of the reference position, a position is preferably used which can be clearly reproduced.

It is likewise possible to use the PET events associated with the time segments in order to create a time segment PET image in the individual time segments, here the time segments 1-6. For instance, only the PET events were taken into account for the time segment PET image 51 which occur during the first recording time frame 25 and in each instance in the first time segment of the cyclical movement. Accordingly, the time segment PET images 52-56 are generated. The previously calculated movement segment information 41-46 can then be applied to the respective time segment PET images 51-56 in order in each instance to generate a corrected time segment PET image 61-66. The movement segment information may be a two or three-dimensional vector field for instance, which describes the movement of the examination object relative to a reference position. In the corrected time segment PET image 61-66, the relative movement of the associated time segment occurring relative to the reference position has then to be taken into account and corrected. In the afore-cited example with the reference position at the end of the exhalation cycle, this would mean that all images 61-66 indicate a PET image of the examination area with a position of the examination area as in the first time segment. If the first sub segment is the reference position for instance, the PET images 62-66 indicate the examination area in the position of the first time segment, since the movement occurring relative to the first time segment was corrected. It is then possible to total the individual time segment PET images in order to form the motion-corrected PET image 70.

The PET image can generally also be used as a basis for the total image, i.e. the reference position, which already comprises the best statistics, i.e. the PET image, which has the majority of PET events within the different time segments of the cyclical movement. When the total required to generate the motion-corrected PET image 70 is formed, the individual time segment PET images 61-66 can be easily totaled. It is furthermore also possible to weight the total as a function of the size of the movement correction. In other words, the greater a movement correction was for generating the time segment PET images, the lower its weighting can be in the total image, in order to reduce the inaccuracies occurring as a result of the movement correction.

Figure 4:
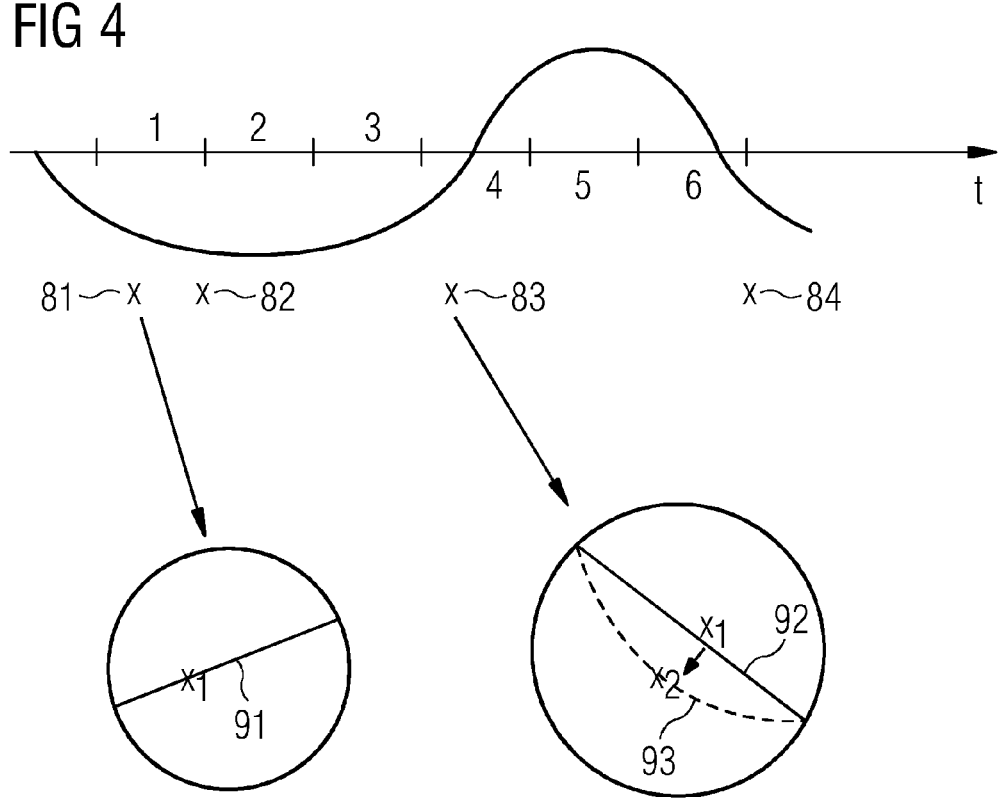
FIG. 4 shows another possibility for determining the motion-corrected PET image, in which the individual PET events are directly taken into account.

A further embodiment is shown in FIG. 4. It is not necessary in this embodiment to generate the time segment PET images associated with the respective time segments. Instead, the PET events and the local information calculated during the PET event are corrected directly. Once again the cyclical respiratory movement is shown in the upper part in FIG. 4, wherein, as in FIG. 3, movement segment information 41-46 likewise exists, which describes the movement of the examination area in the associated time segment relative to a reference position. The PET events 81-84, which appear distributed randomly during the recording time span 25, are detected. The β+-decay occurring during a PET event results, as known, in an annihilation of the positron and the electron, wherein the annihilation beams arising, the two γ-quanta, are irradiated in diametrically opposite directions. The original position of the β+-decay lies on the so-called line of response. Two such lines 91 and 92 are shown in FIG. 4. The line 91 is shown in FIG. 4 for the PET event, wherein it was calculated for instance that the β+-decay has to take place at the position x1. In the example shown, the time segment 1 is in turn the reference position, so that the movement relative to the reference position is determined. The β+-decay 83 arising in time segment 4 is however detected if the examination area has moved. It is estimated from the associated line 92 for instance that the decay must in turn have taken place at the position x1. It is however known from the movement segment information which was determined on the basis of the MR images that the tissue, which was found in time segment 4 at position x1, was actually found in time segment 1 at x2. If the different PET events are now to be totaled directly, this movement can be taken into account such that on account of the MR images, it is known that the tissue which was responsible for the β+-decay and which is mirrored in the PET event 83, is the same tissue which is in the reference time segment at position x2, as shown symbolically by the arrow. This means that with the exemplary embodiment shown in FIG. 4, the measured PET events distribute corresponding movement information on new lines (line of response). To this end, a fractional rebinning is inter alia necessary, which distributes an integral PET event according to the sum on a deformed line, in FIG. 4 in the example shown on line 93.

It is basically possible to reconstruct the 3D PET data recording with a multi ring PET detector by means of a 3D projection. Alternatively to this, the 3D data records can be subjected to a so-called rebinning algorithm. The basic principle here is to calculate and redistribute the 3D data record in an equivalent 2D data record. This can be reconstructed with a correspondingly lower time outlay using an established 2D reconstruction method, such as for instance the filtered reproduction.

Figure 5:
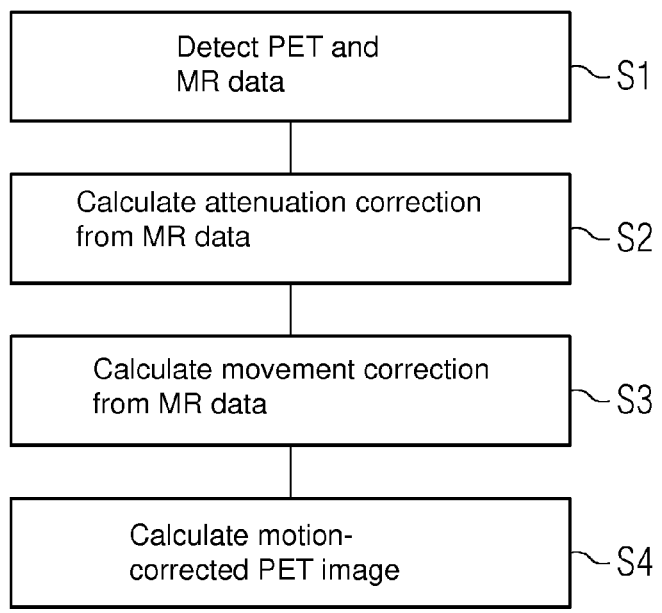
FIG. 5 shows a flow diagram with yet another embodiment for calculating the motion-corrected PET image.

FIG. 5 shows a flow diagram, which shows the steps for calculating a motion-corrected PET image according to an embodiment of the invention. In a first step, the PET and MR data are detected for instance (step S1). It is further possible to use the existing MR images not only for movement correction but instead also for calculating an attenuation correction. The photons arising at a specific point in the tissue pass through tissue and air prior to exiting onto the detector, wherein different tissue types can be passed through. With the aid of the calculated MR images, it is possible in a good resolution to determine the tissue-specific attenuation correction on the path of the photon to the detector. This means that an attenuation correction can be calculated in step S2 with the aid of the MR data. The same MR images, which are used in step S2, can now be used to calculate a movement correction, as was described in detail in FIG. 3 or 4. It is then possible to calculate a motion-corrected PET image with a good signal-to-noise ratio in step S4.

As can be concluded from the above said, the PET events are detected throughout the first time frame. Further, the MR images are recorded at least throughout this first time frame 25. When the detection of the PET events and the acquisition of the MR images is accomplished, it is possible to analyze the cyclic movement, e.g. the respiratory motion. The cyclic movement can then be divided into different time segments so that in each time segment a certain movement has occurred. It is then possible to assign the different PET events which have occurred during the first time frame to the different time segments and to generate a respective time segment PET image using the PET events occurring in the associated time segment. With the present invention, a retrospective correction of the movement is possible as the cyclic movement is determined over the first time frame and based on the patient's respiratory motion. The segmentation into the different time segments can take into account the motion pattern for the examined patient. As the cyclic movement can vary from patient to patient, the cyclic movement can be determined for the examined patient and the motion correction is carried out taking into account the specific motion that occurs during the first time frame where the PET events are recorded. This improves the overall correction of the motion in the PET image.

In summary, a embodiment of the invention allows a PET image to be generated with a high signal-to-noise ratio, since essentially all PET events can be used to generate the PET image and the movement produced during the recording time frame is taken into account. The generated MR images are preferably likewise used to determine the attenuation correction.

One possibility of how a translation, rotation or deformation of a tissue can be determined from the measured MR images, is described for instance in Torsten Rohlfing et al. in "Modeling liver motion and deformation during the respiratory cycle using intensity-based free-form registration of gated MR images", proceedings of SPIE, volume 4319, 2001, the entire contents of which are hereby incorporated herein by reference.

What is claimed is:

1. A method for generating a motion-corrected PET image of an examination area in a combined MR-PET system, the method comprising:
    recording PET events from the examination area in a first recording time frame;
    recording a number of MR images of the examination area in at least the first recording time frame;
    calculating an at least two-dimensional movement information of the examination area on the basis of the recorded number of MR images, wherein the at least two-dimensional movement information describes the movement of the examination area during the first recording time frame, the movement of the examination area being a cyclical movement and the number of MR images are recorded in different time segments of the cyclical movement; and
    determining the motion-corrected PET image from the recorded PET events using the calculated at least two-dimensional movement information, the determining including,
        generating time segment PET images for the different times segments of the cyclical movement, a respective time segment PET image of the time segment PET images is generated on the basis of the PET events occurring in the associated time segment, the generated time segment PET images being associated with movement segment information of the at least two-dimensional movement information, and
        correcting the time segment PET images with the associated movement segment information such that a corrected time segment PET image appears for each time segment of the cyclical movement, in which the movement occurring in the associated time segment is corrected.

2. The method of claim 1, wherein at least two-dimensional movement segment information of the examination area is determined for each of the time segments, which describes the movement of the examination area in the associated time segment.

3. The method of claim 1, wherein the determining includes,
    summing the corrected time segment PET images to generate the motion-corrected PET image.

4. The method of claim 3, wherein the summing is based on sizes of the movement occurring in the time segments, and is the time segment PET images are weighted relatively lower in the summation if the movement was relatively larger in the associated time segment than another time segment PET image, in which the movement was relatively lower in the associated time segment.

5. The method of claim 1, further comprising:
    determining an associated trajectory followed by an annihilation radiation is for each PET event, and the determining the motion-corrected PET image includes,
        calculating corrected trajectories for the PET events with the aid of the two-dimensional movement information, and
        determining the motion-corrected PET image from the corrected trajectories.

6. The method of claim 5, wherein
    the determining the associated trajectory determines deformed trajectories for the PET events on the basis of the at least two-dimensional movement information of the examination area, and
    the determining the motion-corrected PET image includes,
    determining the motion-corrected PET image on the basis of the deformed trajectories.

7. The method of claim 1, wherein the at least two dimensional movement information describes at least one of a translation, rotation and deformation of the examination area.

8. The method of claim 1, wherein the number of MR images is further used to determine an attenuation correction, which is used when determining the motion-corrected PET image.

9. A method for generating a motion-corrected PET image of an examination area in a combined MR-PET system, the method comprising:
   recording PET events from the examination area in a first recording time frame;
   recording a number of MR images of the examination area in at least the first recording time frame;
   calculating an at least two-dimensional movement information of the examination area on the basis of the recorded number of MR images, wherein the at least two-dimensional movement information describes the movement of the examination area during the first recording time frame; and
   determining the motion-corrected PET image from the recorded PET events using the calculated at least two-dimensional movement information, wherein the number of MR images is recorded with a segmented recording technology, in which a cyclical movement of the examination area is monitored and a raw data space of an MR image belonging to a time segment is then only filled with raw data if a specific movement state of the cyclical movement takes place.

10. A combined MR-PET system, configured to generate a motion-corrected PET image of an examination area, the combined MR-PET system comprising:
   a PET unit configured to record PET events from the examination area in a first recording time frame;
   an MR unit configured to record a number of MR images of the examination area in at least the first recording time frame; and
   a computing unit configured to calculate an at least two-dimensional item of movement information of the examination area on the basis of the number of MR images, wherein the movement information describes the movement of the examination area during the first recording time frame, the movement of the examination area being a cyclical movement and the number of MR images are recorded in different time segments of the cyclical movement, and wherein the computing unit is further configured to determine the motion-corrected PET image from the PET events using the calculated movement information, the computing unit further configured to,
      generate time segment PET images for the different times segments of the cyclical movement, a respective time segment PET image of the time segment PET images is generated on the basis of the PET events occurring in the associated time segment, the generated time segment PET images being associated with movement segment information of the at least two-dimensional movement information, and
      correct the time segment PET images with the associated movement segment information such that a corrected time segment PET image appears for each time segment of the cyclical movement, in which the movement occurring in the associated time segment is corrected, the motion-corrected PET image being based on the corrected time segment PET images.

* * * * *